(12) United States Patent
Nakamura

(10) Patent No.: US 8,137,350 B2
(45) Date of Patent: Mar. 20, 2012

(54) FRACTURE FIXATOR FOR FEMORAL TROCHANTERIC FRACTURE

(76) Inventor: Shu Nakamura, Inuyama (JP)

( * ) Notice: Subject to any disclaimer, the term of this patent is extended or adjusted under 35 U.S.C. 154(b) by 288 days.

(21) Appl. No.: 12/445,482

(22) PCT Filed: Sep. 10, 2007

(86) PCT No.: PCT/JP2007/068014
§ 371 (c)(1),
(2), (4) Date: Apr. 14, 2009

(87) PCT Pub. No.: WO2008/047524
PCT Pub. Date: Apr. 24, 2008

(65) Prior Publication Data
US 2010/0023011 A1 Jan. 28, 2010

(30) Foreign Application Priority Data
Oct. 17, 2006 (JP) ................. 2006-309677

(51) Int. Cl.
*A61B 17/76* (2006.01)

(52) U.S. Cl. .......................... 606/65; 606/67

(58) Field of Classification Search .............. 606/62–68, 606/280, 282, 286, 300, 301, 306, 315, 316, 606/323, 329, 328; 411/383, 389, 395
See application file for complete search history.

(56) References Cited

U.S. PATENT DOCUMENTS

| | | | |
|---|---|---|---|
| 5,741,256 A * | 4/1998 | Bresina | 606/62 |
| 5,976,139 A | 11/1999 | Bramlet | |
| 6,319,253 B1 * | 11/2001 | Ackeret et al. | 606/64 |
| 6,695,844 B2 * | 2/2004 | Bramlet et al. | 606/66 |
| 7,632,272 B2 * | 12/2009 | Munro et al. | 606/67 |
| 2001/0049528 A1 * | 12/2001 | Kubota | 606/65 |
| 2007/0123876 A1 * | 5/2007 | Czartoski et al. | 606/62 |
| 2007/0219636 A1 * | 9/2007 | Thakkar | 623/18.11 |
| 2007/0270848 A1 * | 11/2007 | Lin | 606/65 |

FOREIGN PATENT DOCUMENTS

| | | |
|---|---|---|
| FR | 2483214 | 4/1981 |
| FR | 2571957 A1 | 4/1986 |
| JP | 2000515041 | 11/2000 |
| JP | 2005065763 A | 3/2005 |
| WO | 2004107957 A2 | 12/2004 |
| WO | 2008047524 A1 | 4/2008 |

* cited by examiner

*Primary Examiner* — Eduardo C Robert
*Assistant Examiner* — Atiya Mahmud
(74) *Attorney, Agent, or Firm* — Mesmer & Deleault, PLLC

(57) ABSTRACT

In an internal fixator having a sliding mechanism for treating femoral trochanteric fracture, it is intended to firmly hold the femoral head by setting a sliding direction at a high angle. The fixator is constituted of a sliding nail, a femoral head nail, and a sleeve plate. The sliding nail is inserted at a high angle of about 160° in relation to a femoral axis. The femoral head nail is inserted at a low angle of about 95°. A tip of the femoral head nail is located within the femoral head. The femoral head nail is combined and joined with the sliding nail within the bone. A sliding nail passes and slides within the sleeve of the sleeve plate. A sliding direction is consistent with a tangential direction of an inner cortical bone at a fracture side. Thus, displacement between the fracture edges is less likely to occur and excessive shortening can be avoided. With the femoral head nail, the femoral head can be firmly held.

5 Claims, 12 Drawing Sheets

FRACTURE FIXATOR FOR FEMORAL TROCHANTERIC FRACTURE

TECHNICAL FIELD

The present invention relates to a tool used for surgical internal fixation of bone fractures to achieve bone union in femoral trochanteric fracture.

BACKGROUND ART

In a surgical method for femoral trochanteric fracture, an internal fixator referred to as a compression (dynamic) hip screw as shown in FIG. 1 is often used. The compression (dynamic) hip screw is constituted of a sleeve plate 1 and a lag screw 2. The sleeve plate 1 includes a sleeve 3 and a plate 4. The sleeve 3 has a substantially cylindrical shape. The plate 4 is to be secured to femoral diaphysis by screws. The lag screw 2 is configured to firmly hold a femoral head with a screw part thereof, and to slide within the sleeve 3. Thus, compression force is applied to fractured ends to promote bone union.

As shown in FIG. 2, an inner cortical bone 6 at the fracture site has the strongest bone strength in femoral trochanteric fracture (site) 5. The inner cortical bone 6 is the main part to receive a load. In addition, an inner lower part 8 of a femoral head has the densest and strongest bone quality in the cancellous bone of a femoral head 7.

DISCLOSURE OF THE INVENTION

Problems to be Solved by the Invention

During a postoperative period after an operation using a compression hip screw, there are many cases that excessive sliding occurs and shortening develops until a fractured end of a bone fragment on a side of a femoral head is crashed into a cortical bone of a greater trochanter. The shortening may lead to fracture non-union, pain, and weakness in gluteus medius muscle.

The reason for the excessive shortening is considered as follows. In the compression hip screw, a sliding direction 9 of the lag screw 2 is close to an axial direction 10 of a femoral neck portion. The sliding direction 9 is different from a tangential direction 11 of an inner cortical bone at the facture site. Therefore, it often happens that the fractured ends of the inner cortical bone at the fracture site are not engaged well with each other.

An angle between a femoral axis 12 (hereinafter, a caudal side is referred to as an endpoint direction) and the axial direction 10 (the femoral head side is referred to as an endpoint direction) of the femoral neck portion, is about 130°. An insertion angle of the lag screw which determines the sliding direction of the lag screw in the compression hip screw, and an angle between the sleeve and the plate, which corresponds to the insertion angle, are generally 135° and even in a high-angle type, no more than 145°. On the other hand, the tangential direction 11 (the femoral head side is referred to as an endpoint direction) of the inner cortical bone at the facture site in the femoral trochanteric fracture is approximately 160° to 165° in relation to the femoral axis 12.

However, when the lag screw is inserted at a high angle of 150° or more in relation to the femoral axis 12, a tip of the lag screw reaches to an outermost region of the femoral head. Due to bone weakness in the outermost region of the femoral head, if a load is applied thereto, bone around the screw may be destroyed, and fixation force may be lost.

Also, since the sleeve 3 of the compression hip screw is large, it is necessary to drill a bone to form a large insertion hole. The insertion hole and the fracture site are adjacent to each other. Thus, a new bone fracture might be caused during the drilling.

An object of the present invention is, in an internal fixator having a sliding mechanism for treating femoral trochanteric fracture, to firmly hold a femoral head while setting a sliding direction at a high angle in order to avoid excessive shorting.

Means for Solving the Problems

An internal fixator of the present invention is mainly constituted of a sliding nail, a femoral head nail, and a sleeve plate. An angle between a sleeve and a plate of the sleeve plate is about 160°. The sliding nail has a long stick shape and is capable of sliding within the sleeve. The femoral head nail is to firmly hold a femoral head. The femoral head nail and the sliding nail are configured to be combined and joined together within a bone.

A surgical procedure is as follows. A hole is drilled at a high angle of about 160° in relation to a femoral axis. The sliding nail is inserted into the hole. Then, another hole is drilled at a low angle of about 95° in relation to the femoral axis, guided by an angle guide connected to the sliding nail. The femoral head nail is inserted into the drilled hole in such a manner that a tip of the femoral head nail is positioned in a vicinity of an inner lower part of the femoral head. The femoral head nail and the sliding nail are combined together within the bone to be fixed. The sleeve plate is placed at an insertion area for the sliding nail such that the sliding nail can pass within the sleeve of the sleeve plate. Then, the plate part is secured to the femur with screws.

The tip of the femoral head nail is positioned in the vicinity of the inner lower part of the femoral head to receive a load applied to the femoral head. The load transmitted to the femoral head nail is further transmitted to the sliding nail at a joint part with the sliding nail, to produce an acting force for sliding. The sliding direction is a direction determined based on an angle between the plate and the sleeve of the sleeve plate. The sliding direction is at a high angle of about 160° in relation to the femoral axis. The sliding direction is consistent with the tangential direction of the inner cortical bone at the facture site in the femoral trochanteric fracture. As a result, when sliding is performed, fractured ends of the inner cortical bone at the facture site are fitted into each other without causing displacement.

Effect of the Invention

Since the direction of sliding caused by the load is consistent with the tangential direction of the inner cortical bone at the facture site, displacement of fractured ends and excessive shortening are less likely to occur. In addition, a favorable compression force is applied to the fractured ends, so that bone union can be promoted.

A tip part of a sliding nail that is inserted at a high angle is positioned at an outermost region of a femoral head. It is not sufficient to firmly hold the femoral head and receive the load applied to the femoral head only by the sliding nail. However, such insufficiency can be remedied by joining the femoral head nail with the sliding nail and receiving the load.

Insertion of the femoral head nail at a low angle makes it easier to insert the femoral head nail into an inner lower part of the femoral head having the strongest bone quality in a cancellous bone of the femoral head.

Since the insertion hole for the sleeve of the sleeve plate is positioned away from the fracture site, occurrence of another bone fracture during drilling can be avoided. For the same reason, this invention may be applied to a reverse oblique femoral trochanteric fracture.

BEST MODE FOR CARRYING OUT THE INVENTION

The first embodiment of the present invention will be described based on FIGS. 3 and 4. A sliding nail 13 has a long and substantially cylindrical shape. The cylindrical shape in this case includes a polygonal approximate to a cylinder. A substantially rectangular slit 14 is formed in the vicinity of a tip end portion of the sliding nail 13. A femoral head nail is formed into a spiral blade 15. The spiral blade 15 is made of plate-like metal, a tip end of which is in the form of a blade. The plate-like metal is twisted by a quarter turn from a position to be attached to the slit 14, to the tip end of the spiral blade 15. The slit 14 and the spiral blade 15 are similar to each other in cross sectional shape. Therefore, when the spiral blade 15 is inserted into the slit 14, the spiral blade 15 and the slit 14 are connected with each other without looseness. A sleeve plate 16 includes a sleeve part 17 and a plate part 18. An angle between an axial direction of the sleeve 17 and the plate 18 is about 160°. The plate 18 is provided with a plurality of holes into which screws are to be inserted to secure the plate 18 to a femur. The sleeve 17 has a substantially cylindrical shape. An inner diameter of the sleeve 17 is slightly greater than an outer diameter of the sliding nail, so that the sliding nail 13 inserted into the sleeve 17 can slide in a stable manner.

A surgical procedure is as follows. A hole is drilled at an angle of about 160° in relation to a femoral axis to provide an insertion hole for inserting the sliding nail. The sliding nail 13 is inserted into the drilled hole to reach an optimum position. Another hole is drilled with an angle guide connected to the sliding nail 13 to reach an entrance region of the slit 14 in order to provide an insertion hole for inserting the femoral head nail. The drilling direction is at about 95° in relation to the femoral axis. The spiral blade 15 is inserted into the drilled hole, and further inserted by hammering after the spiral blade 15 passes an exit of the slit 14. The sleeve plate 16 is placed such that the sliding nail 13 can be inserted into the sleeve 17 of the sleeve plate 16 to secure the plate 18 to the femur.

The second embodiment of the present invention will be described based on FIGS. 5 and 6. A femoral head nail is formed into a screw 19. A sliding nail 20 has a substantially cylindrical shape and includes a substantially circular hole 21 at an end portion thereof. In the circular hole 21, a female screw is formed by which the screw 19 is fixed when the screw 19 is screwed into the circular hole 21. Screw threads of the screw 19 are thick at a rear portion of the screw 19. Thus, the screw 19 is further stabilized. A sleeve plate 22 is the same in shape as in the first embodiment. A surgical procedure is substantially the same as in the first embodiment. However, an insertion hole for inserting the femoral head nail is drilled for an entire length so that the screw 19 as the femoral head nail is screwed into the circular hole 21.

The third embodiment of the present invention will be described based on FIGS. 7 to 11. A femoral head nail 23 includes a screw portion 24 and a body portion 25. The screw portion 24 and the body portion 25 are capable of being rotated relative to each other as shown in FIG. 9. Moreover, as shown in FIG. 8, the screw portion 24 and the body portion 25 are respectively provided with a projection 26 and a projection 27. When the body portion is rotated, the respective projections are caught with each other at a certain point. As a result, the screw portion is rotated to allow the femoral head nail 23 to move forward and backward within a bone. When the body portion is rotated within a range in which the respective projections are not caught with each other, the body portion 25 is rotated through substantially 360° in relation to the screw portion 24 without allowing the femoral head nail 23 to move forward and backward within the bone. The body portion 25 has a substantially rectangular slit 28 through which the body portion 25 can be connected with an end portion 29 of the sliding nail. The body portion 25 has a substantially rectangular shape. A sleeve plate 30 is the same in shape as in the first embodiment.

A surgical procedure is as follows. A hole is drilled at an angle of about 160° in relation to a femoral axis to provide an insertion hole for inserting the sliding nail. A sliding nail 31 is inserted into the drilled hole to reach a certain position. Another hole is drilled with an angle guide connected to the sliding nail 31 in order to provide an insertion hole for inserting the femoral head nail. After the femoral head nail 23 is inserted into the drilled hole to reach an optimum position, only the body portion 25 is, as explained above, rotated to adjust an angle at which the slit 28 and the end portion 29 of the sliding nail can be joined with each other. Then, the end portion 29 of the sliding nail is inserted into the slit 28. A set screw 32 is inserted into the body portion 25 of the femoral head nail to secure the sliding nail 31 and the femoral head nail 23 with each other. Thereafter, the sleeve plate 30 is secured in the same manner as in the first embodiment.

The fourth embodiment of the present invention will be described based on FIGS. 12 to 15. A femoral head nail 33 includes a screw portion 34 and a body portion 35. The screw portion 34 and the body portion 35 are respectively provided with a projection 36 of the screw portion and a projection 37 of the body portion in the same manner as in the third embodiment. The body portion 35 has a substantially circular hole 38 in which a female screw is formed. An end portion 40 of the sliding nail 39 is formed into a male screw, so that the end portion 40 is connected with the body portion 35 when screwed into the circular hole 38. A sleeve plate 41 is the same in shape as in the first embodiment. A surgical procedure is as follows. In the same manner as in the third embodiment, after the femoral head nail 33 is inserted into a femoral head to reach an optimum position, only the body portion 35 is rotated to be adjusted to an angle at which the circular hole 38 and the end portion 40 of the sliding nail can be joined with each other. Then, the end portion 40 of the sliding nail is screwed into the circular hole 38 to be secured. Thereafter, the sleeve plate 41 is secured in the same manner as in the first embodiment.

The fifth embodiment of the present invention will be described based on FIGS. 16 to 19. A femoral head nail 42 includes a screw portion 43 and a body portion 44 which can be separated from each other. The body portion 44 of the femoral head nail has a cylindrical shape. The body portion 44 includes a screw structure with a small pitch respectively at a front part and a rear part thereof. The screw portion 43 of the femoral head nail is formed into a screw. The screw portion 43 has a circular hole 45 at a rear part thereof. The circular hole 45 has an internal thread therein. At a tip part of a sliding nail 46, a circular hole 47 having a female screw therein is formed. The body portion of the femoral head nail is screwed into and connected with the circular hole 45 and the circular hole 47. A sleeve plate 48 is the same in shape as in the first embodiment.

A surgical procedure is as follows. A hole is drilled at an angle of about 160° in relation to a femoral axis to provide an insertion hole for inserting the sliding nail. The sliding nail 46 is inserted into the drilled hole to reach a certain position. Another hole is drilled with an angle guide connected to the sliding nail 46 in order to provide an insertion hole for inserting the femoral head nail. Only the screw portion 43 of the femoral head nail is inserted into the drilled hole to reach an optimum position. After the sliding nail 46 is inserted such that the circular hole 47 of the sliding nail 46 matches the insertion hole of the femoral head nail, the body portion 44 of the femoral head nail is screwed into the circular hole 45 and the circular hole 47 to secure the sliding nail 46 and the femoral head nail 42 with each other. Thereafter, the sleeve plate 48 is secured in the same manner as in the first embodiment.

DESCRIPTION OF THE NUMERALS

Figure 1:
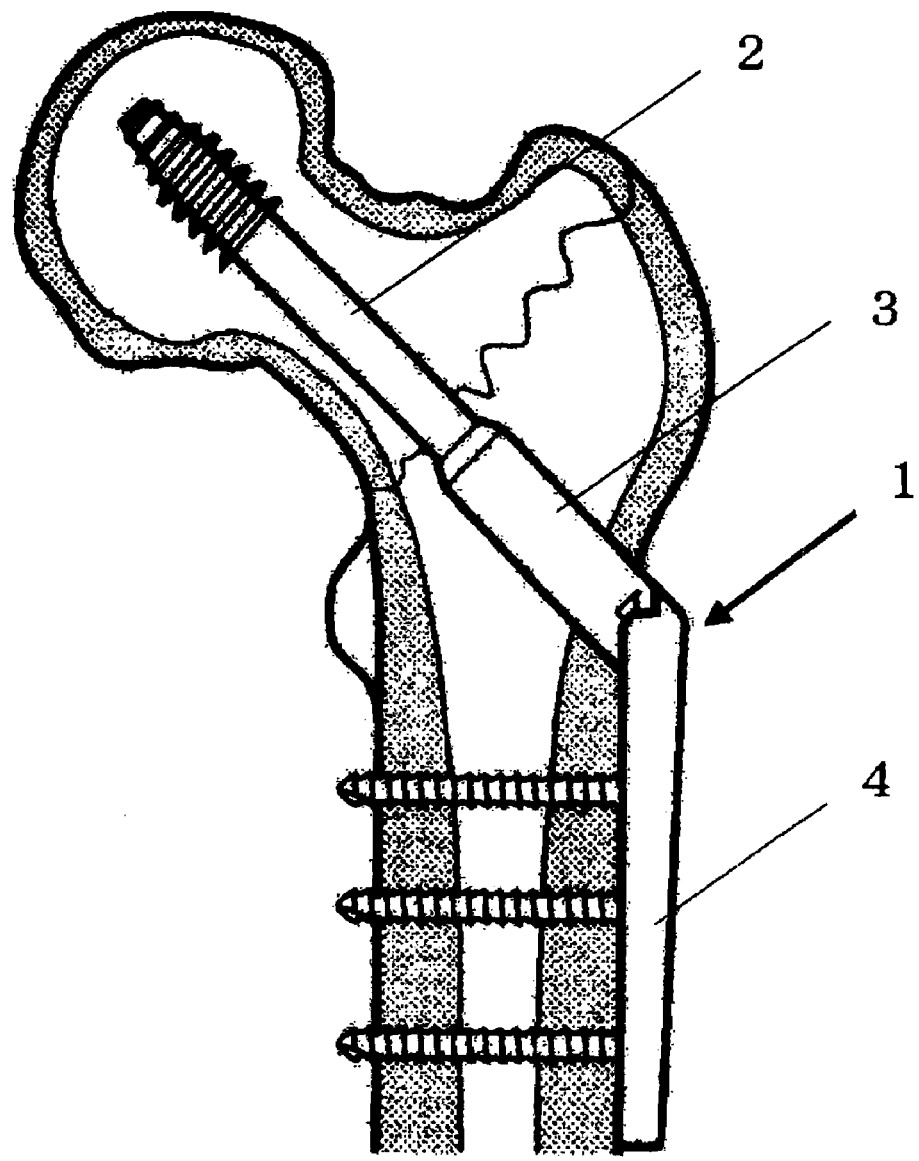
FIG. 1 is a front view of a conventional compression hip screw used for bone fixation.
Figure 2:
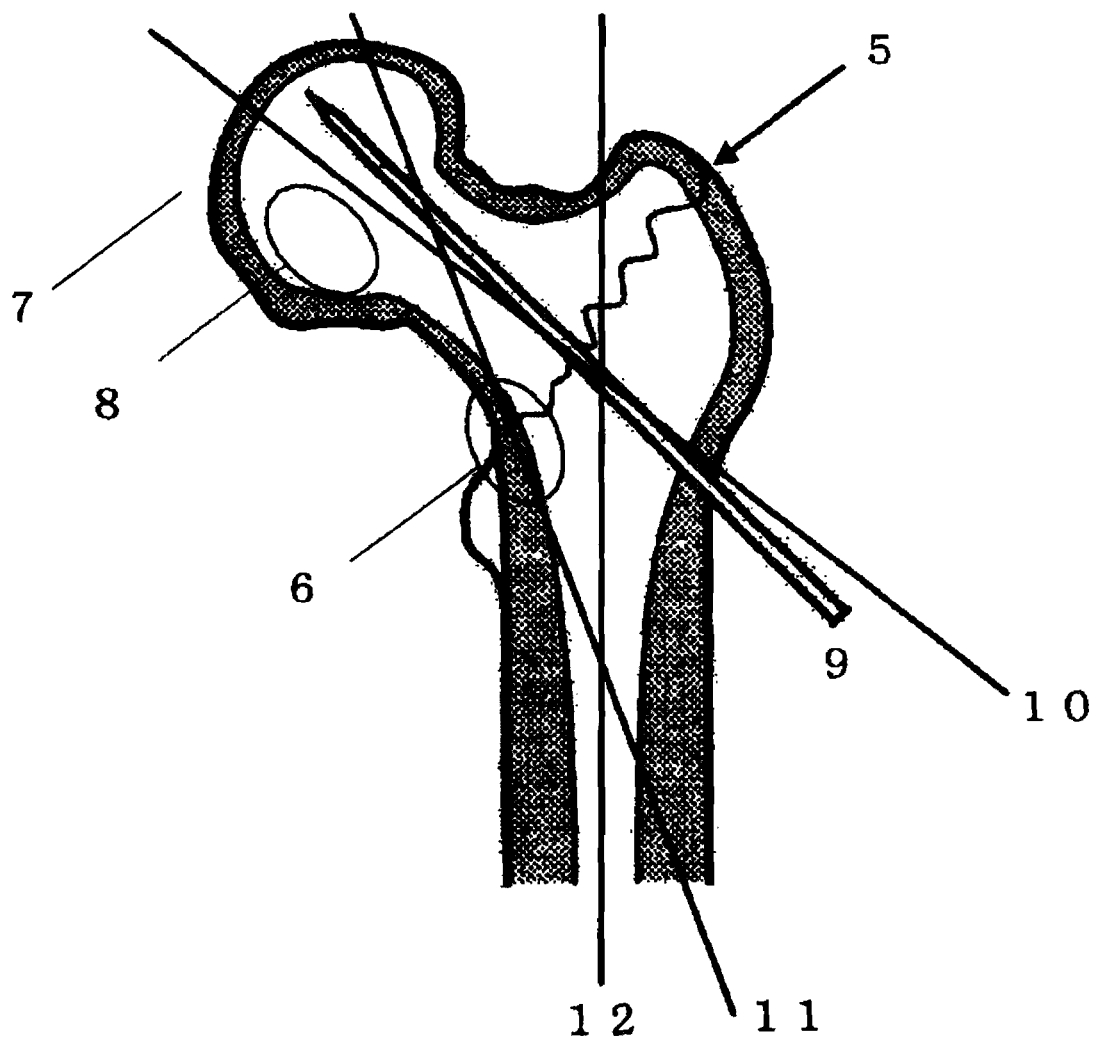
FIG. 2 is a coronal sectional view of a proximal femur.
Figure 3:
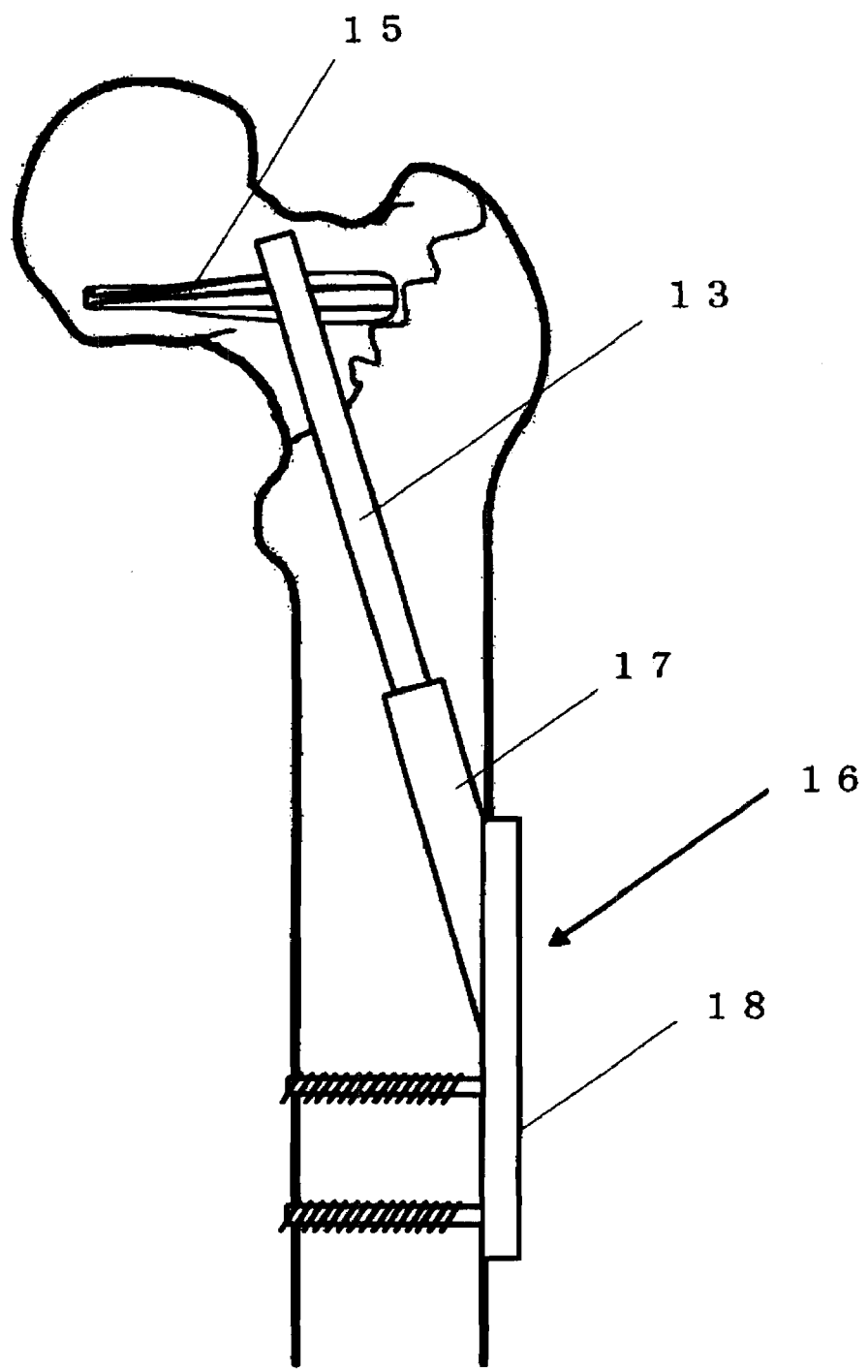
FIG. 3 is a front view of an internal fixator used for bone fixation according to the first embodiment of the present invention.
Figure 4:
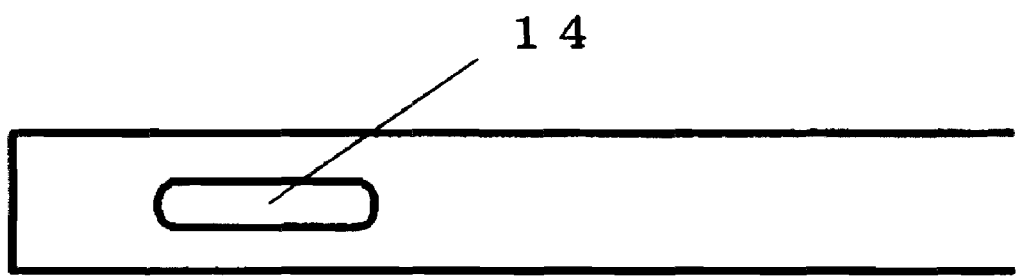
FIG. 4 is a side view of a tip part of a sliding nail according to the first embodiment of the present invention.
Figure 5:
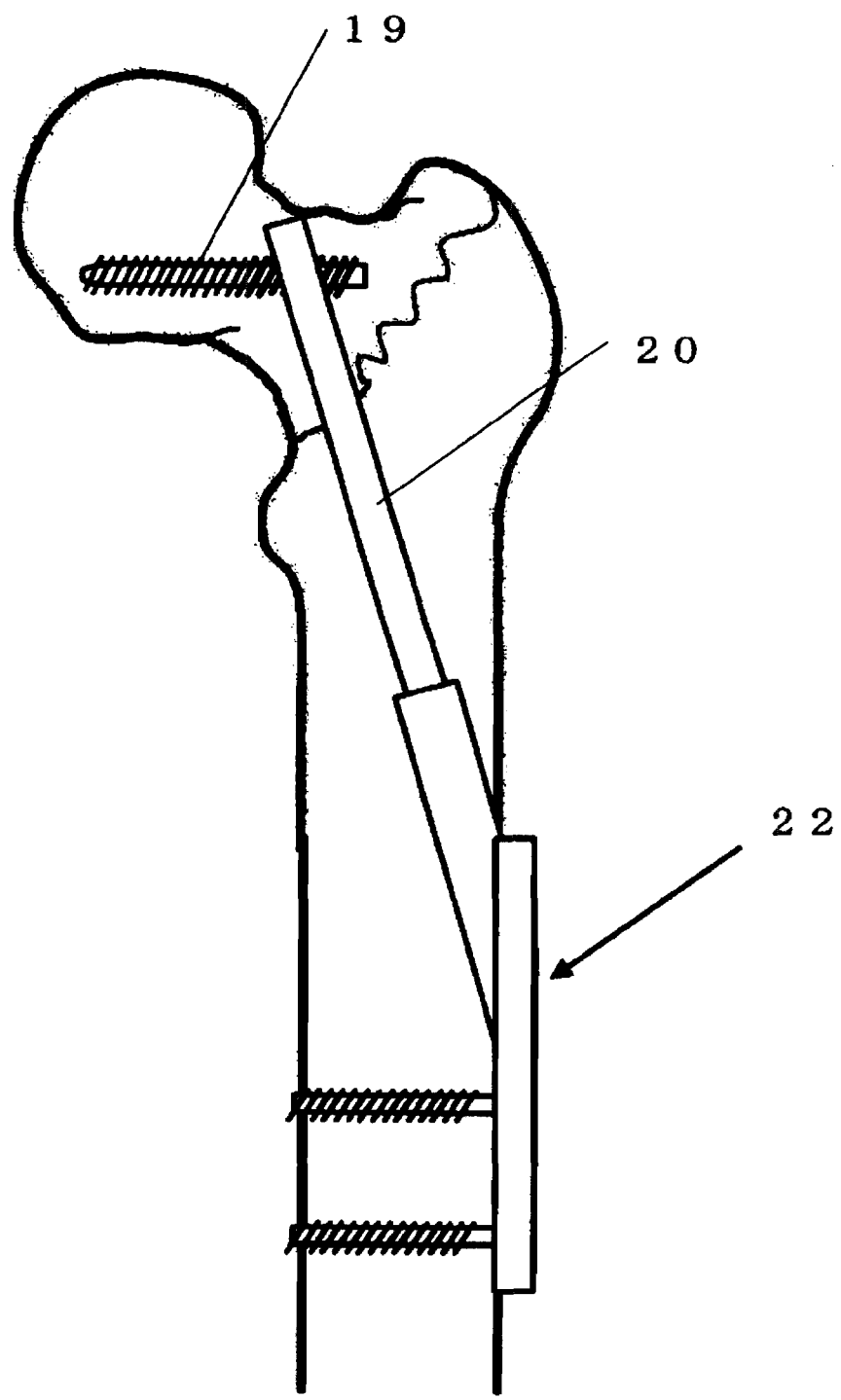
FIG. 5 is a front view of an internal fixator used for bone fixation according to the second embodiment of the present invention.
Figure 6:
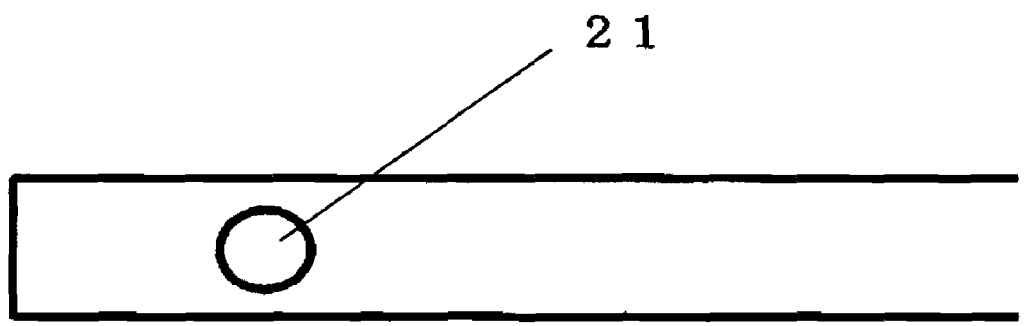
FIG. 6 is a side view of a tip part of a sliding nail according to the second embodiment of the present invention.
Figure 7:
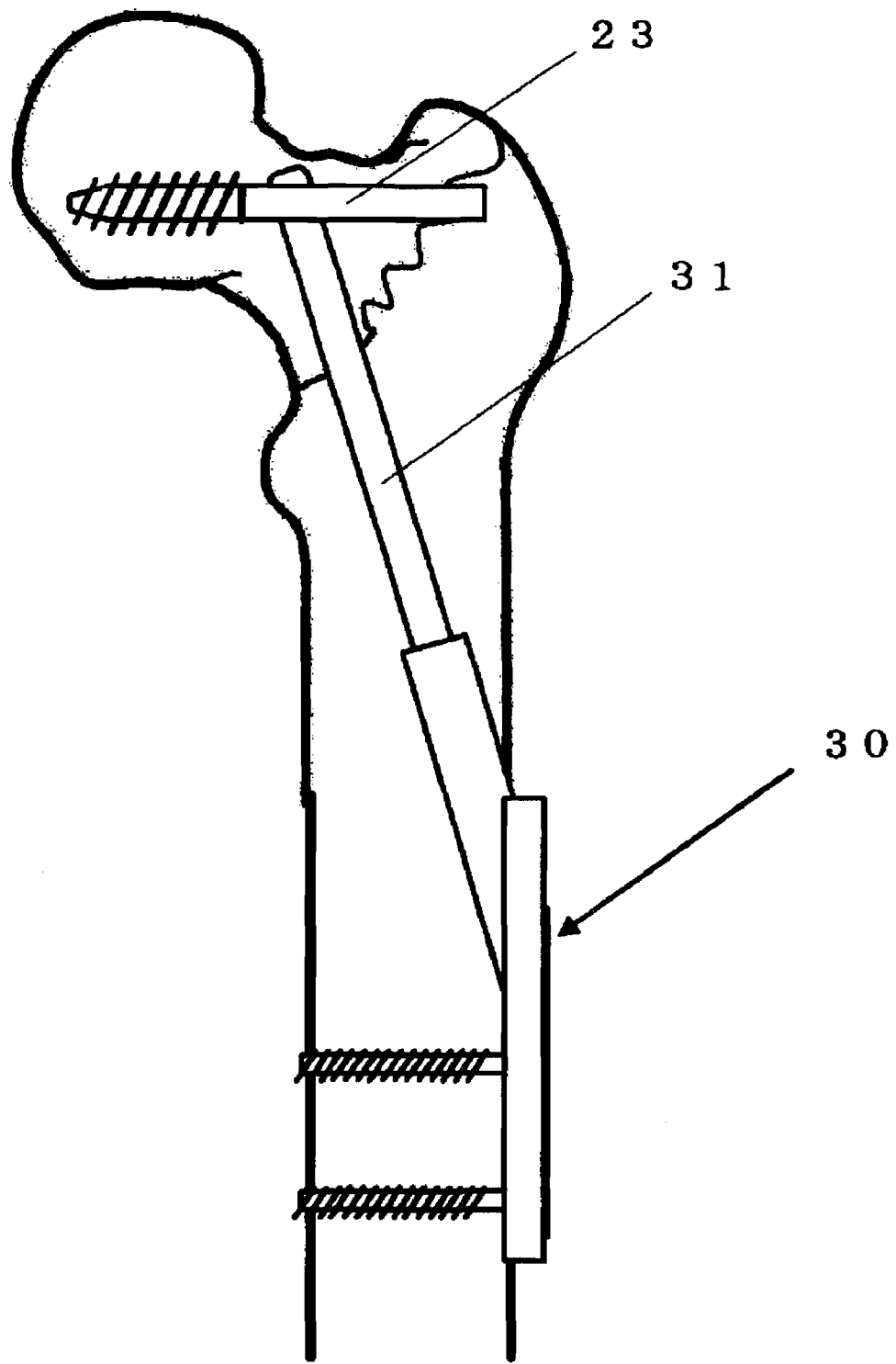
FIG. 7 is a front view of an internal fixator used for bone fixation according to the third embodiment of the present invention.
Figure 8:
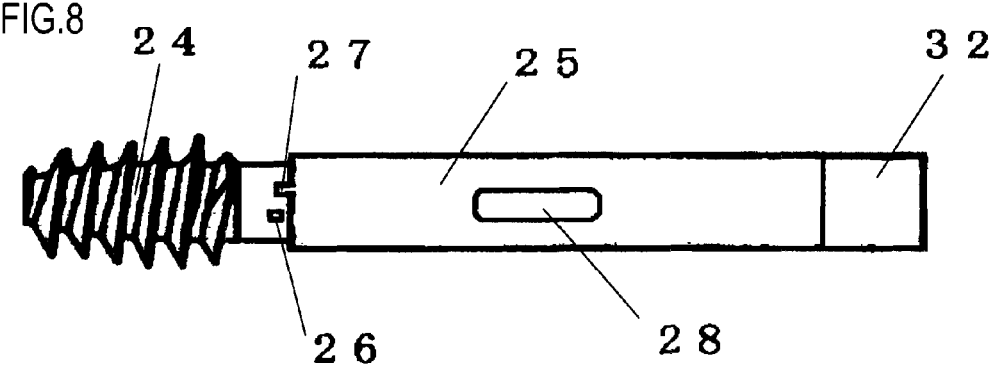
FIG. 8 is a bottom view of a femoral head nail according to the third embodiment of the present invention.
Figure 9:
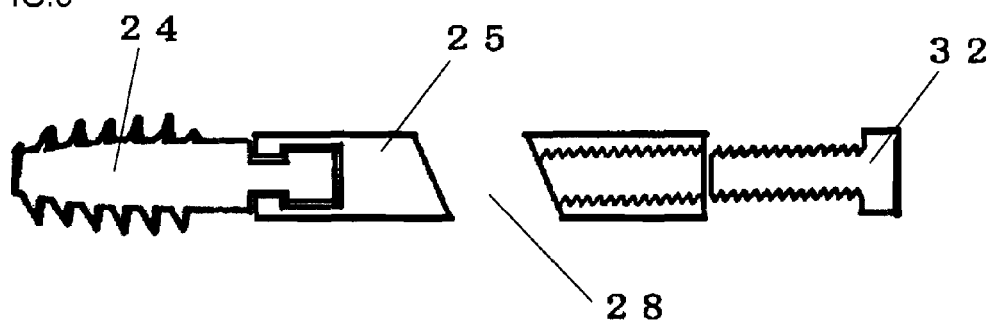
FIG. 9 is a sectional view of the femoral head nail according to the third embodiment of the present invention.
Figure 10:
FIG. 10 is a front view of a tip part of a sliding nail according to the third embodiment of the present invention.
Figure 11:
FIG. 11 is a side view of the tip part of the sliding nail according to the third embodiment of the present invention.
Figure 12:
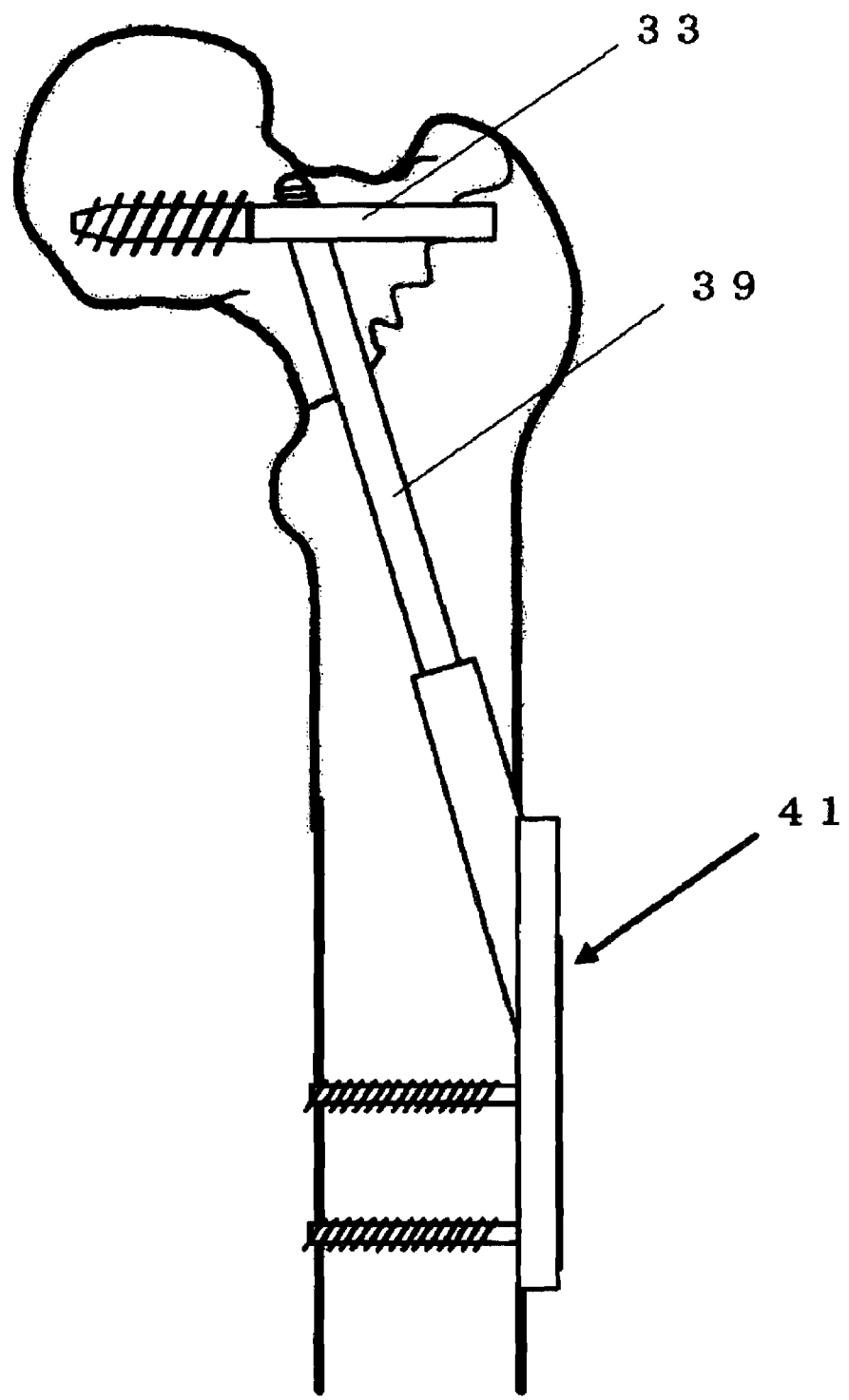
FIG. 12 is a front view of an internal fixator used for bone fixation according to the forth embodiment of the present invention.
Figure 13:
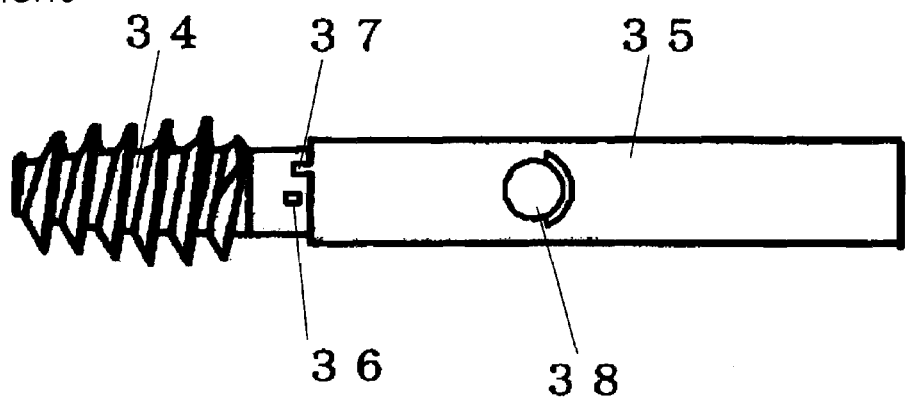
FIG. 13 is a bottom view of a femoral head nail according to the forth embodiment of the present invention.
Figure 14:
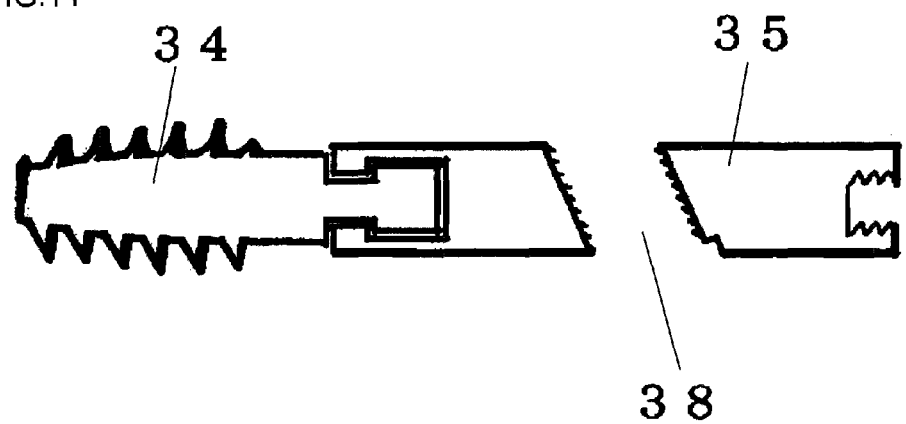
FIG. 14 is a sectional view of the femoral head nail according to the forth embodiment of the present invention.
Figure 15:
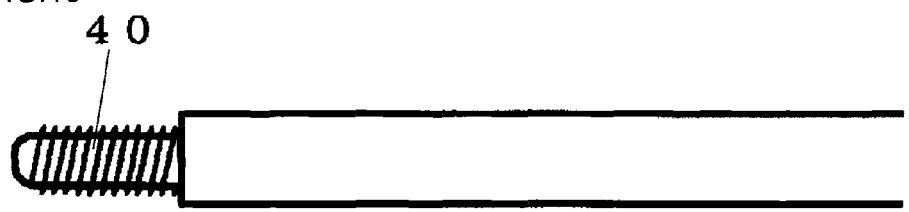
FIG. 15 is a front view of a tip part of a sliding nail according to the forth embodiment of the present invention.
Figure 16:
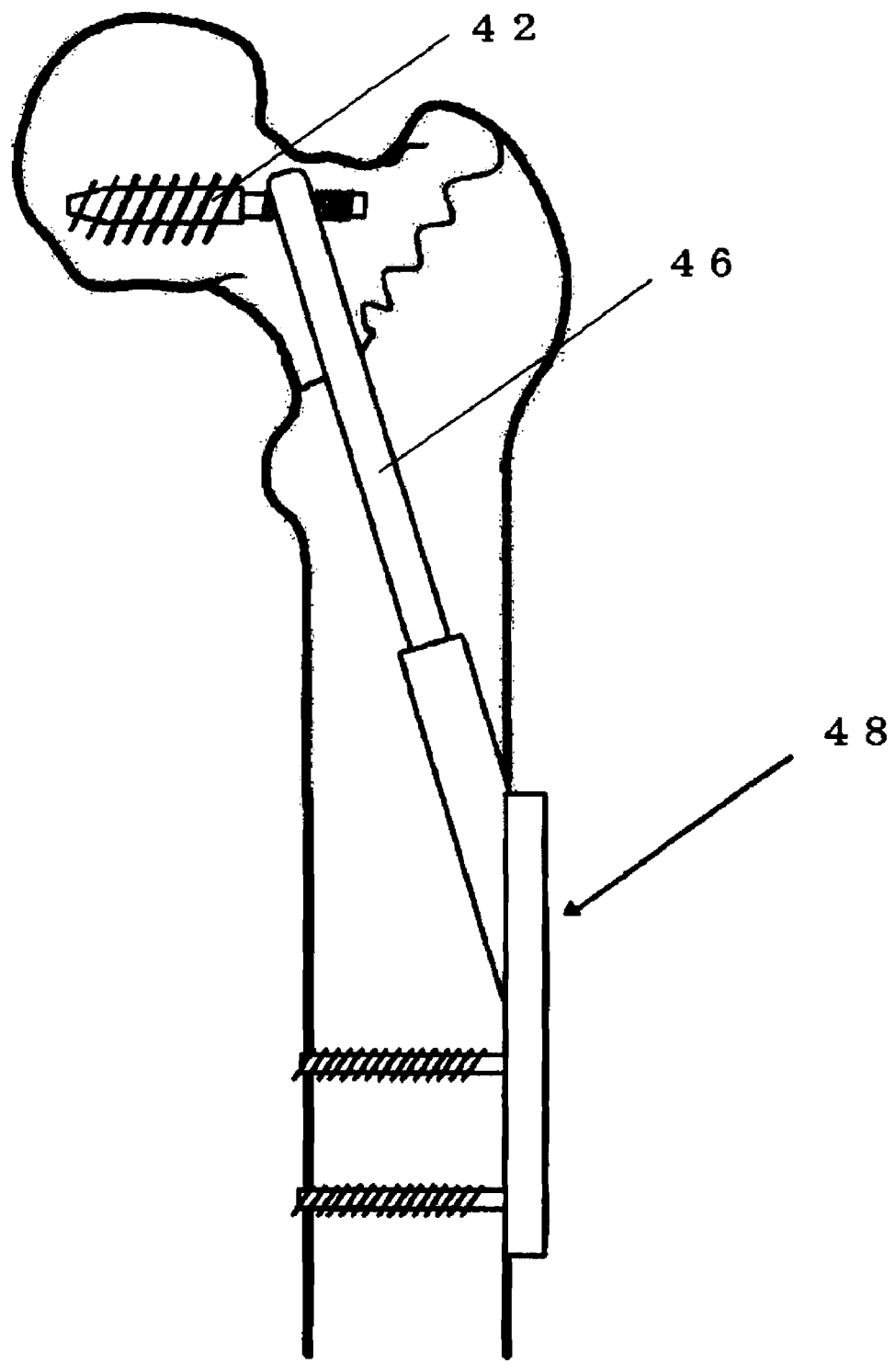
FIG. 16 is a front view of an internal fixator used for bone fixation according to the fifth embodiment of the present invention.
Figure 17:
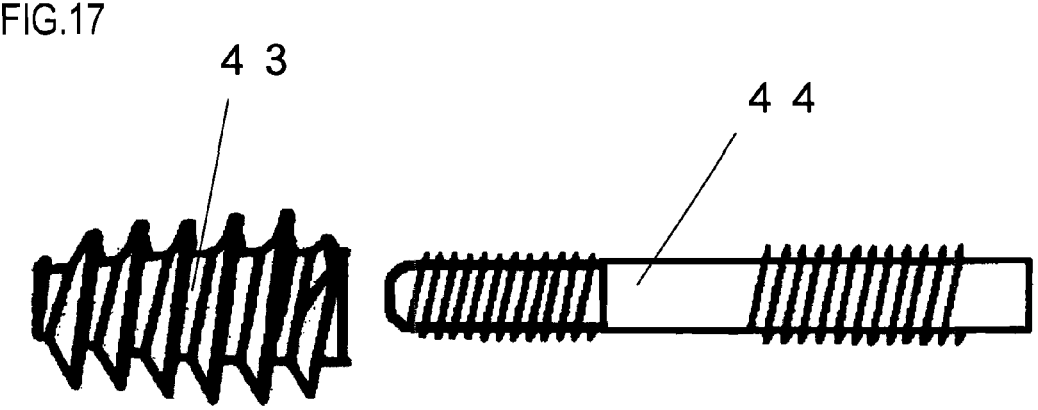
FIG. 17 is a bottom view of a femoral head nail according to the fifth embodiment of the present invention.
Figure 18:
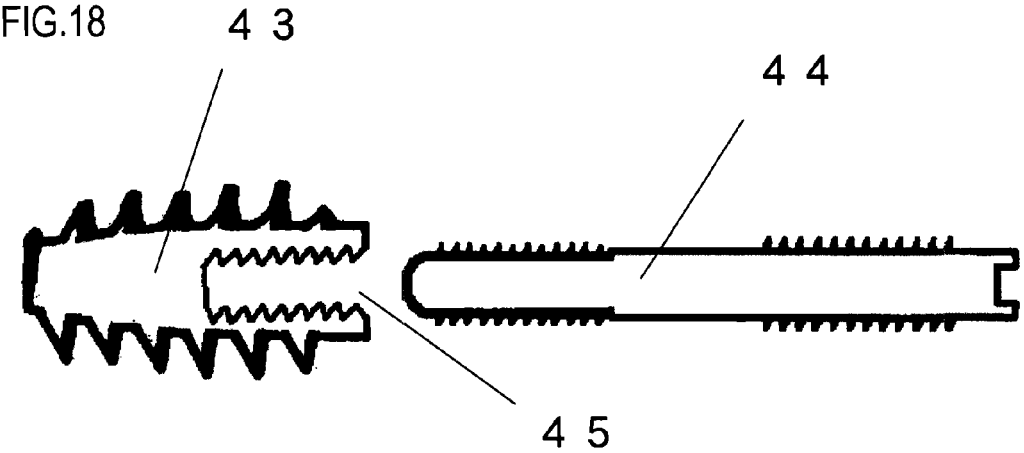
FIG. 18 is a sectional view of the femoral head nail according to the fifth embodiment of the present invention.
Figure 19:
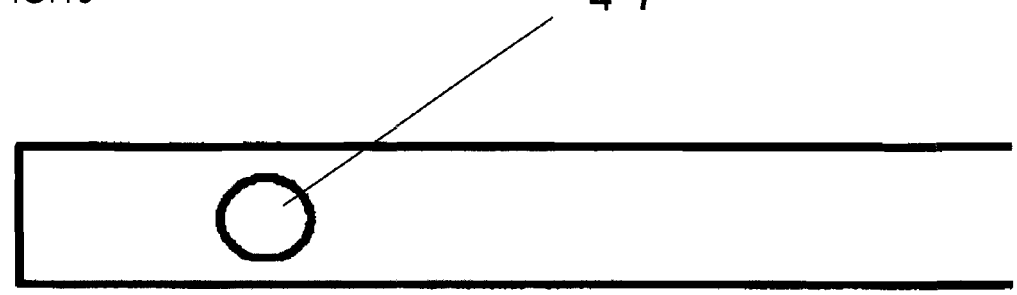
FIG. 19 is a side view of a tip part of a sliding nail according to the fifth embodiment of the present invention.

5 - - - femoral trochanteric fracture (line), 6 - - - inner cortical bone at fracture site, 7 - - - femoral head, 8 - - - inner lower part of femoral head, 9 - - - sliding direction of lag screw, 10 - - - axial direction of femoral neck portion, 11 - - - tangential direction of inner cortical bone at facture site, 12 - - - femoral axis

The invention claimed is:
1. An internal fixator of bone fractures used for fixing a bone fragment on one side of a femoral head with a corresponding bone part on the other side in femoral trochanteric fracture, comprising:
an elongated sliding nail to be inserted into a fractured area from outside of a femoral shaft;
a femoral head nail adapted to be joined with the sliding nail wherein a joining structure is selected from the group consisting of the femoral head nail extending through a through-hole at a tip end portion of the sliding nail and an end portion of the sliding nail extending into a through-hole in a body portion of the femoral head nail such that the femoral head nail and the sliding nail cross each other and wherein the femoral head nail is positioned to be inserted into an inner lower part of the femoral head, the femoral head nail includes a screw portion and a stick-like body portion, the screw portion having a male screw, the body portion receiving one end of the screw portion and rotatably connected relative to the screw portion, wherein the screw portion and the body portion are respectively provided with projections, the projections being brought into contact with each other at a predetermined rotation angle when the screw portion and the body portion are relatively rotated, and wherein the body portion has a through hole for receiving a tip part of the sliding nail to join the sliding nail and the femoral head nail with each other; and
a sleeve plate having a securing part and a sleeve part, the securing part to be secured to the femoral shaft on the outside of the femoral shaft, and the sleeve part to be projecting from the securing part and slidably receiving the sliding nail in an elongated direction of the sliding nail,
wherein with the securing part being secured to the femoral shaft, the sleeve part is configured to project in a direction at a high angle of 136° or more in relation to a femoral axis, assuming that a caudal direction of the femoral axis is defined as 0° and
wherein the femoral head nail, when joined with the sliding nail, is configured to be inserted at a lower angle than the high angle in relation to the femoral axis to reach within the femoral head, so as to firmly hold the bone fragment on the side of the femoral head.

2. The internal fixator of bone fractures according to claim 1 wherein a male screw is formed on the tip part of the sliding nail, wherein the through hole of the body portion is formed with a female screw that is capable of being screwed together with the male screw formed on the sliding nail, and wherein the male screw of the sliding nail and the female screw of the body portion are configured to be screwed together, so that the sliding nail and the femoral head nail are joined with each other.

3. The internal fixator of bone fractures according to claim 1, wherein the body portion has a fixing female screw as a female screw that is communicated with the through hole of the body portion, wherein there is provided a male screw member which is configured to be screwed into the fixing female screw such that the male screw member is reached to the through hole of the body portion, and wherein the male screw member is configured to be screwed with the fixing female screw and brought into contact with the sliding nail inserted into the through hole of the body portion, so that the sliding nail and the femoral head nail are secured to each other.

4. The internal fixator of bone fractures according to claim 1, wherein the body portion has a fixing female screw as a female screw that is communicated with the through hole of the body portion, wherein there is provided a set screw which is configured to be screwed into the fixing female screw such that the male screw member is reached to the through hole of the body portion, and wherein the set screw is configured to be screwed with the fixing female screw and brought into contact with the sliding nail inserted into the through hole of the body portion, so that the sliding nail and the femoral head nail are secured to each other.

5. The internal fixator of bone fractures according to claim 1, wherein with the securing part being secured to the femoral shaft, the sleeve part is configured to project in a direction at an angle of about 160° in relation to the femoral axis, assuming that the caudal direction of the femoral axis is defined as 0°, so as to receive the sliding nail.

* * * * *